(12) United States Patent
Leonard Neethling et al.

(10) Patent No.: US 9,205,172 B2
(45) Date of Patent: Dec. 8, 2015

(54) IMPLANTABLE BIOMATERIAL AND A METHOD OF PRODUCING SAME

(75) Inventors: William Morris Leonard Neethling, Booragoon (AU); Andrew Julian Hodge, Winthrop (AU)

(73) Assignee: ADMEDUS REGEN PTY LTD, Perth (AU)

(*) Notice: Subject to any disclaimer, the term of this patent is extended or adjusted under 35 U.S.C. 154(b) by 2442 days.

(21) Appl. No.: 11/316,584

(22) Filed: Dec. 21, 2005

(65) Prior Publication Data
US 2006/0193885 A1 Aug. 31, 2006

(51) Int. Cl.
*A61F 13/00* (2006.01)
*A61L 27/36* (2006.01)
*A61L 27/58* (2006.01)

(52) U.S. Cl.
CPC ............. *A61L 27/3687* (2013.01); *A61L 27/58* (2013.01); *A61L 2400/02* (2013.01)

(58) Field of Classification Search
CPC .. A61L 27/3687; A61L 27/58; A61L 2400/02
See application file for complete search history.

(56) References Cited

U.S. PATENT DOCUMENTS 5,188,834 A * 2/1993 Grimm et al. ............... 424/422
5,746,775 A * 5/1998 Levy et al. ................... 8/94.11
7,008,763 B2 * 3/2006 Cheung ......................... 435/1.1
7,022,348 B2 * 4/2006 Ketharanathan ............. 424/569
7,550,152 B2 * 6/2009 Pandit et al. ................. 424/423

FOREIGN PATENT DOCUMENTS

WO    WO 84/01894    5/1984

OTHER PUBLICATIONS

Neethling et al., J Heart Valve Dis. Jul. 2004;13(4):689-96.*
Weissenstein et al., J Heart Valve Dis. Mar. 2000;9(2):230-40, Abstract Only.*
Vyavahare et al., Circulation.1997;95:479-488 (cited in Applicant's IDS of Feb. 22, 2006).*
Stacchino et al., (J Heart Valve Dis. Mar. 1998;7(2):190-4, Abstract Only).*
Pathak et al., (Apr. 2004), "Treatment of bioprosthetic heart valve tissue with long chain alcohol solution to lower calcification potential", Biomed Mater Res A. 1; 69(1):140-4.
Vyavahare et al., (1997), "Prevention of Bioprosthetic Heart Valve Calcification by Ethanol Preincubation: Efficacy and Mechanisms", Circulation, 95, p. 479-488.

* cited by examiner

*Primary Examiner* — Cherie M Stanfield
(74) *Attorney, Agent, or Firm* — Locke Lord LLP; Jeffrey D. Hsi

(57) ABSTRACT

The present invention relates to an implantable biomaterial and methods of producing same. In particular, the present invention relates to a method for producing an implantable biomaterial comprising (a) exposing a biomaterial to an alcohol-containing solution for at least 24 hours.

24 Claims, 6 Drawing Sheets

IMPLANTABLE BIOMATERIAL AND A METHOD OF PRODUCING SAME

RELATED APPLICATION

This application claims priority under 35 USC §120 to Australian Provisional patent application AU2004907348 filed on Dec. 23, 2004.

FIELD

The present invention relates to an implantable biomaterial and methods of producing same. In particular, the invention relates to a method of treating a collagen-containing biomaterial to reduce and/or alleviate calcification and improve longevity of the biomaterial, which can be used on or with an implantable device and methods of producing same.

BACKGROUND

There are numerous methods for chemically changing and/or fixing the collagenous matrix of biological tissues to enable such tissues to be implanted into a living mammalian body. Examples of changed and fixed implantable biological tissues include cardiac valves, blood vessels, pericardium, skin, dura mater, tendons and ligaments.

These biological tissues consist mainly of collagen and elastin. The rigidity/elasticity of most biological tissues is largely determined by the relative collagen and elastin content in the tissues and/or the physical configuration of the connective tissue framework.

Each collagen molecule consists of three polypeptide chains intertwined to form a coiled triple helix. Chemical agents used to preserve biological tissues generally form cross-links between amino groups situated on the polypeptide chains within a collagen molecule (intramolecular) as well as between adjacent collagen molecules (intermolecular).

Collagen-based biomaterials, when used as implantable devices in different recipient species, are prone to hyperacute rejection. This hyperacute rejection is a natural immunological response, triggered by antigens present in the structure of the collagen-based biomaterial. Hyperacute rejection is a rapid degenerative process, which affects the function and durability of such an implantable device.

The antigenicity of collagen-based biomaterials can be suppressed by physical or chemical cross-linking of the collagen. Physical cross-linking methods such as ultraviolet irradiation or thermal dehydration results in low density cross-linking. Chemical agents such as formaldehyde, glutaraldehyde, dialdehyde starch and certain polyepoxy compounds have been used as chemical cross-linking agents in collagen-based biomaterials.

Cross-linking collagen involves the reaction of a cross-linking agent with amine groups of lysine or hydroxylysine residues on different polypeptide chains. Another known method of cross-linking collagen is to activate the carboxyl groups of glutamic and aspartic acid residues in a polypeptide chain to react with the amine groups of another polypeptide chain to form amide bonds.

Cross-linking can also be performed by bridging amine groups of adjacent polypeptide chains with diisocyanates, which results in the formation of urea bonds. This method is less popular due to the toxicity and the low solubility of most diisocyanates.

In recent times, glutaraldehyde has been the cross-linking agent of choice. Glutaraldehyde is rendered bifunctional due to the presence of an aldehyde present at both ends of a five carbon aliphatic chain. Apart from fixing the tissue, glutaraldehyde is an excellent sterilising agent for preparing biological tissues for implantation.

In particular, permanently implantable biomaterials, which have been fixed with glutaraldehyde, include porcine bioprosthetic heart valves, bovine pericardial valves and bovine pericardial patches.

A problem associated with the implantation of biological materials, cross-linked with chemical agents, is that these materials, specifically the collagen and elastin in these materials, tend to calcify. Calcification of these materials can result in stiffening which result in degradation and failure of the material. It is known that both extrinsic and intrinsic calcification is responsible for the calcification of cross-linked biomaterials.

Unfortunately, glutaraldehyde is known to promote calcification in biomaterials. Reaction of aldehyde and primary amines in the biomaterials form unstable imines (Schiff base) which subsequently release glutaraldehyde from the biomaterial. Unbound aldehydes present in the tissue can cause severe tissue irritations, such as inflammatory reactions, after implantation. There is therefore a need to remove or inactivate the calcification-promoting effects of cross-linking agents such as glutaraldehyde.

The mechanism of calcification of cross-linked biomaterials has not yet been fully understood. Clinical data have shown that factors such as patient age, infection, host tissue chemistry, dehydration, distortion, dietary factors and inadequate initial anticoagulation therapy can promote calcification of implanted biomaterials.

Many attempts have been undertaken to find ways to mitigate the calcification of cross-linked biomaterials. Research on the mitigation of calcification of biomaterials has primarily focussed on the treatment of the cross-linked biomaterials and is described in, but not limited to, U.S. Pat. No. 4,553,974 (Dewanjee et al.); U.S. Pat. No. 4,120,649 (Schechter); U.S. Pat. No. 4,648,881 (Nashef et al.); and U.S. Pat. No. 4,976,733 (Girardot) Vyavahare et al., 1997, *Circulation*, 95:479-488 and Pathak et al., 2004, *J. Biomed. Mater Res.*, 69A: 140-144. These publications generally describe methods of treating fixed tissues with alcohol before implantation. In other words, the tissue has already been cross-linked before being exposed to alcohol. Even in instances where tissues are pre-incubated in the presence of alcohol, the period of exposure is often too short to be useful or the presence of buffer and other agents adversely affects the cross-linking stability (see, for example, Vyavahare et al., 1997, supra). Alternative processes to fix biomaterials with non-glutaraldehyde reagents have also been described and these include, but are not limited to, the use of polyglycidal ethers (Imamura et al., (1988), *Jpn. J. Artif. Organs*, 17:1101-1103); photo-oxidation (Moore et al., (1994), *J. Biomed. Mater. Res.*, 28:611-618).

Treatment of cross-linked biomaterials with amino-diphosphate and surfactant has demonstrated reduced calcification in these biomaterials after implantation. However, these agents tend to wash out of the biomaterial after implantation and only delay the calcification process.

The use of alcohol in the treatment of biomaterials is well known, but is limited to its use as a solvent and/or sterilising agent. For example, the use of alcohol in the treatment of biomaterials against pathologic calcification is limited to its use in previously cross-linked collagenous biomaterials; U.S. Pat. No. 5,746,775 (Levy et al.) and International Pat. No. WO84/01894.

Consequently, there still exists a need for a method of producing a biomaterial that has a long-term resistance to calcification.

SUMMARY

The inventors have developed methods that overcome or at least alleviate the problems of calcification with collagen-containing implantable biomaterials.

Accordingly, in a first aspect the present invention provides a method for producing an implantable biomaterial comprising:

(a) exposing a biomaterial to an alcohol-containing solution for at least 24 hours.

In a second aspect, the present invention provides a method of treating a collagen containing biomaterial to produce calcification resistant biomaterial comprising:

(a) exposing a biomaterial to an alcohol-containing solution for at least 24 hours.

In some embodiments, the method of the first and second aspects further comprise the steps:

(b) exposing said material in step (a) to a cross-linking agent; and (c) exposing said material in step (b) to an acidic solution; wherein step (b) and (c) are sequential to step (a).

While it is preferred that step (a) is carried out for at least 24 hours, more preferably at least 36 hours and most preferably, at least 48 hours, it will be appreciated by those skilled in the art that in some circumstances step (a) may be carried out for a shorter time period.

Accordingly, in a third aspect the present invention provides a method for producing an implantable biomaterial comprising:

(a) exposing a biomaterial to an alcohol-containing solution;

(b) exposing said material in step (a) to a cross-linking agent; and (c) exposing said material in step (b) to an acidic solution; wherein step (b) and (c) are sequential to step (a).

In a fourth aspect, the present invention provides a method of treating a collagen containing biomaterial to produce calcification resistant biomaterial comprising:

(a) exposing a biomaterial to an alcohol-containing solution;

(b) exposing said material in step (a) to a cross-linking agent; and (c) exposing said material in step (b) to an acidic solution; wherein step (b) and (c) are sequential to step (a).

In some embodiments, between steps (a) and (b) and/or between steps (b) and (c) of the methods of the invention the biomaterial or collagen containing material is rinsed to remove residual alcohol and/or cross-linking agent. Preferably, the biomaterial or collagen containing material is further rinsed after step (c) to remove residual acidic solution.

It will be appreciated by those skilled in the art that the methods disclosed herein may be useful for treating any biomaterial. Preferably, the biomaterial comprises collagen.

In some embodiments, the biomaterial is a cultured tissue, a prosthesis containing extra-cellular matrix obtained from an animal, a reconstituted tissue (e.g. collagen matrix), or the like.

It will also be appreciated that the biomaterial might comprise synthetic analogs formed from synthetic polymers, biological polymers, or both, including those generally found in natural tissue matrices. Suitable synthetic polymers include, for example, polyamides and polysulphones. Biological polymers can be naturally occurring or produced in vitro by, for example, fermentation and the like.

In some embodiments, the biomaterial is naturally occurring and has been isolated from an animal. The biomaterial can be isolated from any animal, whether from the same species as a recipient or from an animal of a different species to the recipient. Preferably, the animal is from one of the mammalian orders i.e. *Artiodactyla, Lagomorpha, Rodentia, Perissodactyla, Carnivora* and *Marsupialia*. More preferably, the animal is selected from the group consisting of an ovine, a bovine, a caprine, an equine, a porcine, a marsupial and a human.

The biomaterial may be any type of cellular tissue. Preferably, the cellular tissue is selected from the group consisting cardiovascular tissue, heart tissue, heart valve, aortic roots, aortic wall, aortic leaflets, pericardial tissue, connective tissue, dura mater, dermal tissue, a vascular tissue, cartilage, pericardium, ligament, tendon, blood vessels, umbilical tissue, bone tissue, fasciae, and submucosal tissue and skin.

In some embodiments, the biomaterial is and/or comprises discrete i.e. isolated collagen rather than a naturally-occurring collagen-containing tissue. The discrete collagen may be used in its isolated state or formed into any medical device or article known in the art.

The biomaterial used in step (a) has not been previously cross-linked.

The alcohol-containing solution used in step (a) is preferably a liquid, and is water-based i.e. is an aqueous solution of greater than about 50% alcohol, and preferably between 60% to 80% alcohol by volume. Either buffered or non-buffered alcohol-containing solution can be used; however, it is preferable that a non-buffered alcohol-containing solution is used as it has been found that buffered alcohol-containing solutions adversely affect subsequent cross-linking procedures producing a yellowed biomaterial.

The methods of the invention can use any alcohol known in art in the alcohol-containing solution. Preferably, the alcohol is a $C_1$-$C_6$ lower alcohol in a buffer-free solution. Even more preferably, the alcohol is selected from the group consisting of methanol, ethanol, cyclohexanol, isopropanol, propanol, butanol, pentanol, isobutanol, sec-butanol and t-butanol.

In some embodiments, the alcohol-containing solution comprises a mixture of two or more alcohols provided that the combined volume of the alcohol is greater than 50%. For example, a mixture of about 70% ethanol and about 10% isobutanol is effective.

The biomaterial in step (a) can be exposed to the alcohol-containing solution for any length of time as long as it is sufficient to render the biomaterial resistant to in vivo pathogenic calcification. Preferably, the biomaterial remains in contact with the alcohol-containing solution for sufficient time to enable the alcohol to diffuse and permeate into the biomaterial. More preferably, the biomaterial is exposed to the alcohol-containing solution for at least 24 hours, even more preferably at least 36 hours and most preferably, at least 48 hours.

In some embodiments, e.g. those in which the biomaterial has been exposed to the alcohol-containing solution for greater than 24 hours, the biomaterial may be used directly in the treatment methods of the invention disclosed infra.

In some embodiment, the biomaterial, after exposure to the alcohol-containing solution, is removed and exposed to one or more cross-linking agents. Any form of cross-linking agent known in the art or combination thereof may be used as long as it is capable of cross-linking collagen. Accordingly, it will be appreciated that cross-linking agents, include but are not limited to, divinyl sulfone (DVS), polyethylene glycol divinyl sulfone (VS-PEG-VS), hydroxyethyl methacrylate divinyl sulfone (HEMA-DIS-HEMA), formaldehyde, glutaraldehyde, aldehydes, isocyanates, alkyl and aryl halides, imidoesters, N-substituted maleimides, acylating compounds, carbodiimide, hydroxychloride, N-hydroxysuccinimide, light (e.g., blue light and UV light), pH, temperature, and combinations thereof. Preferably, the cross-linking agent is a chemical cross-linking agent selected from the group consisting of carbodiimide, polyepoxy ethers, divinyl sulfone (DVS), polyaldehyde and diphenylphosphoryl azide (DPPA).

In some embodiments, the polyaldehyde is a bi-, tri- or di-aldehyde. Glutaraldehyde is especially preferred.

In some embodiments, the cross-linking step (b) is followed by step (c), with or without an intervening wash step. The acidic solution used in step (c) contains any acid capable of inactivating and/or modifying the fixed and/or unfixed cross-linking agent moieties present in the biomaterial after step (b) to remove or reduce available calcium binding sites. Alternatively, or in addition to, the acidic solution used in step (c) contains any acid capable of further cross-linking the activated carboxyl groups with the activated amine groups on the collagen to form amide bonds. Preferably, the acid in the acidic solution comprises an aminocarboxylic acid. Preferably, the aminocarboxylic acid is an acid having at least one amino group and at least one carboxylic acid substituent. More preferably, the aminocarboxylic acid is selected from the group consisting of L-arginine, L-lysine, L-histidine, L-glutamate or L-aspartate.

In some embodiments, step (c) of the disclosed methods is replaced by or supplemented with a method of inhibiting the formation of metalloproteinase on elastin molecules present in the biomaterial. Specifically, in tissue such as aortic tissue a higher percentage of elastin is present than in other tissue. These elastin molecules can provide sites for the formation of metalloproteinase as such these sites need to be reduced, removed or inactivated. As shown in Example 1 infra, a buffer-free solution, containing a multi-valent cation such as magnesium, ferric and aluminium salts can be used to reduce the formation of metalloproteinase.

The step of rinsing the biomaterial is conducted using a phosphate-free solution of 0.9% saline.

In one preferred embodiment, the biomaterial after step (c) is further sterilised. More preferably, the biomaterial is sterilised after being rinsed.

While it will be appreciated by those skilled in the art that the temperature at which each of the steps of the present invention is carried out is not critical, it will be understood that preferably, the temperature is between 2° C. and 40° C., more preferably, between 4° C. and 30° C. and most preferably, between 5° C. and 25° C.

In one embodiment, the alcohol, cross-linking agent and acidic solution, rinsing solution and sterilizing solution are all buffer-free.

It will be appreciated by those skilled in the art that the methods disclosed herein are capable of producing a calcification-resistant biomaterial, which retains less than 50 µg of calcium per mg of tissue for greater than 200 days post in vivo implantation. In other words, the calcification-resistant biomaterial of the present invention is capable of being implanted for greater than 200 days without the biomaterial increasing its calcium content above 50 µg/mg of tissue.

Accordingly, in a fifth aspect the present invention provides a calcification resistant biomaterial comprising cross-linked collagen, wherein said biomaterial has a calcium content of less than about 50 µg per mg of biomaterial and wherein said biomaterial is capable of being implanted for at least 200 days without the biomaterial increasing its calcium content above 50 µg/mg of biomaterial.

Without wishing to be bound by any theory or hypothesis it is considered that the calcification resistant observed is brought about in part by the presence of secondary amines in the collagen brought about by the methods of producing the biomaterial as disclosed herein.

Accordingly, in a sixth aspect, the present invention provides an implantable biological device comprising a calcification resistant biomaterial comprising cross-linked collagen, wherein said collagen comprises secondary amines.

In some embodiments, the calcification resistant biomaterial is coated onto a surface of a medical device. In a further embodiment, the device further comprises at least a second coating.

It will be appreciated by those skilled in the art, that the at least second coating can comprise agents such as anti-microbial agent, anti-viral agents, growth factors, anti-dehydration agents or anti-septic agents.

Preferably, the anti-microbial agent is selected from the group consisting of isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ampicillin, amphotericin B, ketoconazole, fluconazole, pyrimethamine, sulfadiazine, clindamycin, lincomycin, pentamidine, atovaquone, paromomycin, diclazaril, acyclovir, trifluorouridine, foscarnet, penicillin, gentamicin, ganciclovir, iatroconazole, miconazole, Zn-pyrithione, heavy metals including, but not limited to, gold, platinum, silver, zinc and copper, and their combined forms including, salts, such as chloride, bromide, iodide and periodate, and complexes with carriers, and other forms.

Preferably, the growth factor agent is selected from the group consisting of hydroxyapatite, basic fibroblast growth factor (bFGF), acidic fibroblast growth factor (aFGF), nerve growth factor (NGF), epidermal growth factor (EGF), insulin-like growth factors 1 and 2, (IGF-1 and IGF-2), platelet derived growth factor (PDGF), tumor angiogenesis factor (TAF), vascular endothelial growth factor (VEGF), corticotropin releasing factor (CRF), transforming growth factors α and β (TGF-α and TGF-β) interleukin-8 (IL-8); granulocyte-macrophage colony stimulating factor (GM-CSF); interleukins, and interferons.

In some embodiments, the device of the present invention further comprises a bioabsorbable material selected from the group consisting of polylactic acid, polyglycolic acid, polylactic acid—polyglycolic acid copolymers, polydioxanone, polycaprolactone, polypeptides, polycarbonates, polyhydroxybutyrate, poly(alkylene oxalate), copolymers of vinyl acetates with unsaturated carboxylic acids, water soluble or dispersible cellulose derivatives, ethylene oxide polymers, polyacrylamide, collagen, gelatin, poly(orthoester), polyamides of amino acids, polyvinyl alcohol, polyvinyl pyrrolidone, polyetheretherketone, tricalcium phosphate, and mixtures thereof.

It will be appreciated that the devices of the present invention can be any device for which calcification resistance would be desirable. Preferably, the device is selected from the group consisting of an artificial heart, an extracardiac compression device, an intra or extravascular compression device, a heart valve prosthesis, an annuloplasty ring, a dermal graft, a vascular graft, a vascular stent, a structural stent, a vascular shunt, a cardiovascular shunt, a dura mater graft, a cartilage graft, a cartilage implant, a pericardium graft, a ligament prosthesis, a tendon prosthesis, a urinary bladder prosthesis, a pledget, a suture, a permanently in-dwelling percutaneous device, a surgical patch, a cardiovascular stent, a coated stent and a coated catheter. More preferably, the device is a heart valve prosthesis.

In some embodiments, the device will further comprise a tissue fragment harvested from an animal or a synthetic analog of a tissue.

Preferably, the tissue fragment will include a plurality of cells, which, upon implantation at a surgical site, will proliferate and integrate into the surrounding tissue.

In a seventh aspect, the present invention provides a biocompatible implant, comprising a biocompatible scaffold comprising a calcification-resistant biomaterial comprising cross-linked collagen, wherein said biomaterial has a calcium content of less than about 50 µg per mg of biomaterial and wherein said biomaterial is capable of being implanted for at least 200 days without the biomaterial increasing its calcium content above 50 µg/mg of biomaterial.

In an eighth aspect, the present invention provides a biocompatible implant, comprising a biocompatible scaffold comprising a calcification-resistant biomaterial comprising cross-linked collagen, wherein said collagen comprises secondary amines.

Preferably, the implants of the present invention will further comprise a synthetic polymer, a natural polymer, an injectable gel, a ceramic material, autogeneic tissue, allogeneic tissue, xenogeneic tissue and combinations thereof.

In a ninth aspect, the present invention provides a kit for repairing a tissue injury, comprising:
(a) a sterile container having one or more calcification resistant biomaterials comprising cross-linked collagen, wherein said collagen comprises secondary amines; and
(b) instructions for use on an injured subject.

In a tenth aspect, the present invention provides a method of treating living tissue, comprising:
(a) providing a calcification resistant biomaterial comprising cross-linked collagen, wherein said collagen comprises secondary amines; and
(b) implanting the biomaterial in or on a subject in need of treatment.

The method of treatment may be any treatment, include prophylactic and therapeutic treatments. Preferably, the method of treatment is selected from the group consisting of tissue repair, deep tissue protection, tissue bulking, cosmetic treatment, therapeutic treatment, tissue augmentation, and tissue sealing.

In an eleventh aspect, the present invention provides a wound dressing comprising a calcification resistant biomaterial comprising cross-linked collagen, wherein said collagen comprises secondary amines.

Preferably, the collagen in the biomaterial is selected from the group consisting of ovine collagen, bovine collagen, caprine collagen, equine collagen, porcine collagen, marsupial collagen and human collagen.

In some embodiments, the wound dressing further comprises a sulphated polysaccharide selected from the group consisting of heparin, chondroitin sulphate, dextran sulfate, dermatan sulfate, heparan sulfate, keratan sulfate, hexuronyl hexosaminoglycan sulfate, inositol hexasulfate, and sucrose octasulfate. Preferably, the wound dressing further comprises an anti-microbial agent, an anti-viral agent, a growth factor, an anti-dehydration agent or an anti-septic agent.

Preferably, the biomaterial comprises at least 50% collagen, more preferably, at least 70% collagen, even more preferably, at least 90% collagen and most preferably, consists essentially of collagen.

DETAILED DESCRIPTION OF THE PREFERRED EMBODIMENTS

Figure 1:
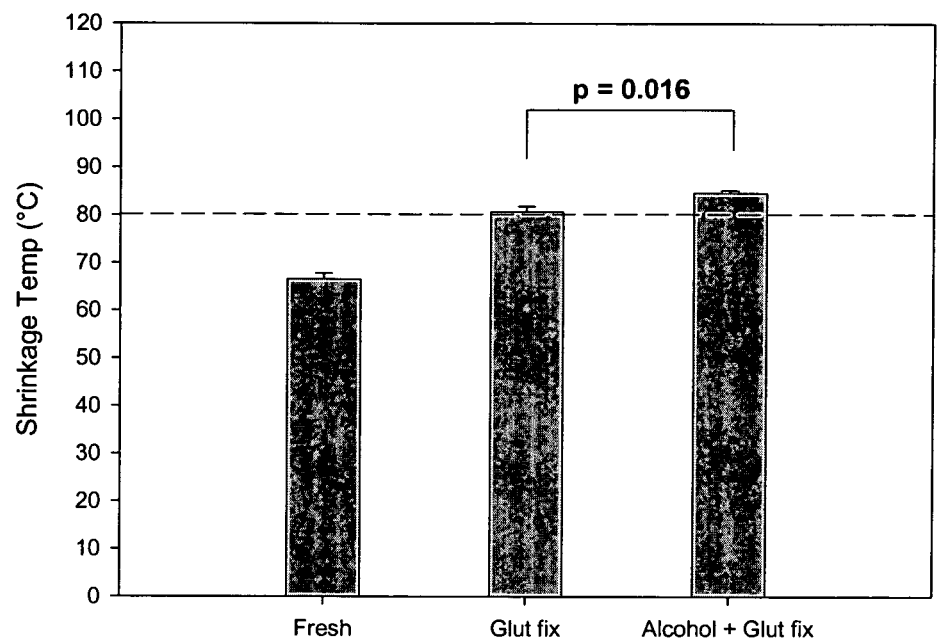
FIG. 1 shows kangaroo pericardium tissue that was pretreated with alcohol then glutaraldehyde fixed compared to glutaraldehyde fixed tissue i.e. no alcohol pre-treatment and "fresh" tissue.

Before describing the present invention in detail, it is to be understood that this invention is not limited to particularly exemplified methods of production, which may, of course, vary. It is also to be understood that the terminology used herein is for the purpose of describing particular embodiments of the invention only, and is not intended to be limiting which will be limited only by the appended claims.

All publications, patents and patent applications cited herein, whether supra or infra, are hereby incorporated by reference in their entirety. However, publications mentioned herein are cited for the purpose of describing and disclosing the protocols and reagents which are reported in the publications and which might be used in connection with the invention. Nothing herein is to be construed as an admission that the invention is not entitled to antedate such disclosure by virtue of prior invention.

Furthermore, the practice of the present invention employs, unless otherwise indicated, conventional immunological techniques, chemistry and pharmacology within the skill of the art. Such techniques are well known to the skilled worker, and are explained fully in the literature. See, e.g., Coligan, Dunn, Ploegh, Speicher and Wingfield "Current protocols in Protein Science" (1999) Volume I and II (John Wiley & Sons Inc.); and Bailey, J. E. and Ollis, D. F., Biochemical Engineering Fundamentals, McGraw-Hill Book Company, NY, 1986; Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986).

It must be noted that as used herein and in the appended claims, the singular forms "a," "an," and "the" include plural reference unless the context clearly dictates otherwise. Thus, for example, a reference to "a cross-linking agent" includes a plurality of such agents, and a reference to "an alcohol" is a reference to one or more alcohols, and so forth. Unless defined otherwise, all technical and scientific terms used herein have the same meanings as commonly understood by one of ordinary skill in the art to which this invention belongs. Although any materials and methods similar or equivalent to those described herein can be used to practice or test the present invention, the preferred materials and methods are now described.

In one of the broadest aspects, the present invention relates to a method for producing an implantable biomaterial.

As used herein, the term "biomaterial" refers to any material that potentially has a biological use, wherein the material comprises some collagen. The collagen might be any type of collagen from any source and might be present alone or in combination with other materials. Accordingly, the collagen might represent as little as 1% w/w of the total weight of the biomaterial or as much as 100%.

The term "collagen" as used herein refers to the extracellular family of fibrous proteins that are characterised by their stiff, triple-stranded helical structure. Three collagen polypeptide chains ("α-chains") are wound around each other to form this helical molecule. The term is also intended to encompass the various types of collagen.

The major portion of the helical portion of collagen varies little between mammalian species. Indeed, a number of collagen types have high degrees of nucleotide and amino acid sequence homologies. For example, the nucleotide sequence homology for collagen alpha I type II is at least 88% when comparing humans, equines and murine. Humans and equines have 93% sequence homology at the nucleotide level, while mouse and equine have 89% sequence homology. The nucleotide sequence homology for human and mouse is 88% (see, NCBI accession numbers U62528 (Equine), NM033150 (Human) and NM031163 (mouse) www.ncbi.nlm.nih.gov). Other types of collagen have similar levels of amino acid homology. For example, the nucleotide sequence homology between porcine collagen alpha I type I and ovine collagen alpha I type I is 90% (see, NCBI accession numbers AF29287 (Ovine) and AF201723 (Porcine) www.ncbi.nlm.nih.gov).

Given the level of common ancestry and biology for many of the above animals, the high degree of amino acid and nucleotide sequence homology for collagen across a number of species such as cattle, sheep, mice and pigs, a person skilled in the art would appreciate that the methods for producing the biomaterial as disclosed herein are applicable for collagenous material isolated from all mammalian animals.

Accordingly, in some embodiments, the biomaterial is isolated or harvested from an animal of one of the mammalian orders i.e. *Artiodactyla, Lagomorpha, Rodentia, Perissodactyla, Carnivora* and *Marsupialia*. The animal is preferably an ovine, a bovine, a caprine, an equine, a porcine, a marsupial or a human. While the biomaterial is preferably isolated from the same animal species as the recipient, it is envisaged that the biomaterial might be isolated from a different species to the recipient.

Alternatively, in some embodiments, the biomaterial comprises a cultured tissue, a reconstituted tissue or the like.

The biomaterial might be any type of cellular tissue. For example, the cellular tissue might be cardiovascular tissue, pelvic floor tissue, heart tissue, heart valve, aortic roots, aortic wall, aortic leaflets, pericardial tissue, connective tissue, the matrix of soft or solid organs, dura mater, dermal tissue, a vascular tissue, dura mater, cartilage, pericardium, ligament, tendon blood vessels, umbilical tissue, bone tissue, fasciae, and submucosal tissue or skin as all of these comprises some collagen.

It will also be appreciated that the biomaterial might further comprise synthetic analogs formed from synthetic polymers, purified biological polymers, or both, including those generally found in natural tissue matrices. Suitable synthetic polymers include, for example, polyamides and polysulphones. Biological polymers can be naturally occurring or produced in vitro by, for example, fermentation and the like.

Purified biological polymers can be appropriately formed into a substrate by techniques such as weaving, knitting, casting, moulding, extrusion, cellular alignment, and magnetic alignment. Suitable biological polymers include, without limitation, collagen, elastin, silk, keratin, gelatin, polyamino acids, polysaccharides (e.g. cellulose and starch), and copolymers of any of these. For example, collagen and elastin polymers can be formed into a synthetic implantable material by any of a variety of techniques, such as weaving and moulding. Synthetic tissue analogs mimic a natural tissue matrix. Alternatively, synthetic substrates can be used to form a tissue analog, either alone or together with naturally occurring substrates Non-limiting examples include, polypropylene, polylactic acid, polyester, nylon, silicone and the like.

It will be appreciated that while the methods disclosed herein might have some effect on previously cross-linked biomaterial the methods disclosed herein are intended to be used on uncross-linked i.e. "native" or "naive" material.

Once the biomaterial has been acquired, it is prepared for implantation. The terms "implantation," "implantable," and "implant" are used herein interchangeably and all refer to the ability of the biomaterial, devices et cetera of the present invention to be placed within or onto living tissue of an animal without leading to rejection, infection or toxic problems. It should be understood that the term "implantable" can include a partially of biomaterials or devices and also includes partially implanted devices et cetera such as contact lenses and the like.

In an initial step of the methods of the present invention the biomaterial is exposed to an alcohol-containing solution. As used herein, the term "exposed," or "exposing" refers to the active step of contacting the biomaterial or a collagen containing material with an alcohol-containing solution as described here, or as described infra, subsequently containing the biomaterial with cross-linking agent, acidic solution or other matter for a sufficient period of time to bring about a desired outcome. Methods for exposing the biomaterial to, for example, the alcohol-containing solution are well known in the art. For example, in general, the biomaterial can be "exposed" to alcohol, by spraying, dipping or immersing the biomaterial in a solution comprising an alcohol.

The term "alcohol" as used herein refers to any alcohol known in art which is capable of removing or reducing the amount of triglycerides and at least partially esterifying the carboxyl groups found on collagen. Preferably, the alcohol is a water-soluble alcohol. More preferably, the alcohol is a $C_1$-$C_6$ lower alcohol in a buffer-free solution. Even more preferably, the alcohol is selected from the group consisting of methanol, ethanol, cyclohexanol, isopropanol, propanol, butanol, pentanol, isobutanol, sec-butanol and t-butanol.

Without wishing to be bound by any particular theory or hypothesis the inventors consider that the alcohol-containing solution assists in loosening the collagen triple helix and thereby exposing hydrophobic sites (see, Karube & Nishida, 1979, *Biochim Biophys Acta.*, 23; 581(1): 106-13). They also consider that the carboxyl and amine groups found in collagen are esterified in the presence of the alcohol-containing solution such that they become available for cross-linking in later steps. As such, a preferred alcohol solution is one comprising at least about 50% v/v, more preferably at least about 70% v/v and most preferably at least about 80% v/v alcohol to buffer-free aqueous solution. In one embodiment, the alcohol solution is 70% ethanol v/v in 0.9% saline (containing 0.5 mM PMSF)

In one embodiment the method of the present invention provides a method for producing an implantable biomaterial comprising exposing a biomaterial to an alcohol-containing buffer-free solution comprising less than 100% alcohol for at least 24 hours.

In some embodiments the alcohol-containing solution, as well as other solutions and reagents are "buffer-free" as it is hypothesised that the cross-linking agents containing aldehyde reacts with the buffer during fixation causing depolymerization of the aldehyde.

The step of exposing the biomaterial to the alcohol-containing solution may be carried out for any length of time as long as it is sufficient to render the biomaterial resistant to in vivo pathogenic calcification and that the majority (i.e. a high percentage) of the carboxyl and amine groups found in collagen are esterified. Preferably, the biomaterial remains in contact with the alcohol-containing solution for sufficient time to enable the alcohol to diffuse and permeate into the biomaterial. More preferably, the biomaterial is exposed to the alcohol-containing solution for at least 24 hours, even more preferably at least 36 hours and most preferably, at least 48 hours.

Once the biomaterial has been exposed to alcohol it is removed. In some embodiments, the biomaterial is rinsed after the exposure to alcohol in a rinsing solution comprising a phosphate-free solution of 0.9% saline. However, any non-buffered physiologically acceptable solution may be used as a rinsing solution. The purpose of the rinsing solution is mainly to remove excess alcohol and as such is not critical.

After the biomaterial or collagen containing material has been exposed to alcohol for greater than 24 hours, it can be used directly for implantation. While alcohol pre-fixation has been used previously by others it has traditionally been used to sterilise tissue rather than esterification of the carboxyl and amine groups found in collagen. As such, the time of exposure to alcohol has been relatively short e.g. less than 24 hours and not sufficient to enable the full penetration of the tissue by the alcohol. As a result there has been no appreciation, prior to the present invention, that a calcification-resistant biomaterial (see definition infra) could be produced by prolonged i.e. greater than 24 hour, exposure of a biomaterial to an alcohol-containing solution. This means that the biomaterial, after exposure to the alcohol-containing solution for greater than 24 hours, could be implanted directly (described infra) as a calcification-resistant biomaterial. However, it will be appreciated by those skilled in the art that a superior form of calcification-resistant biomaterial can be produced by cross-linking the biomaterial after step (a).

Accordingly, in some embodiments of the present invention the biomaterial or collagen containing material after exposure to alcohol is then exposed to one or more bifunctional cross-linking agents. The term "bifunctional" as used herein refers to the two functional aldehyde groups, present at both ends of the five carbon chain. The cross-linking can be undertaken by any technique known in the art, with any form of cross-linking agent as long as it is capable of cross-linking collagen. Cross-linking agents, include but are not limited to, acylating compounds, adipyl chloride, aldehydes, alkyl and aryl halides, bisimidates, carbodiimides, divinyl sulfone (DVS), formaldehyde, glutaraldehyde, glyoxal, hexamethylene diisocyanate, hydroxychloride, hydroxyethyl methacrylate divinyl sulfone (HEMA-DIS-HEMA), imidoesters, isocyanates, light (e.g. blue light and UV light), N-hydroxysuccinimide, N-substituted maleimides, pH, polyaldehyde, diphenylphosphoryl azide (DPPA), polyepoxy compounds comprising backbone of 17-25 carbons and 4-5 epoxy groups, polyepoxy ethers, polyethylene glycol divinyl sulfone (VS-PEG-VS), polyglycerol polyglycidyl ether and temperature and combinations thereof.

In some embodiments, the cross-linking agent is a chemical cross-linking agent such as carbodiimide, polyepoxy ethers, divinyl sulfone (DVS), genipin, glutaraldehyde, formaldehyde and diphenylphosphoryl azide (DPPA).

It has also been demonstrated that polyepoxy compounds comprising backbone of 17-25 carbons and 4-5 epoxy groups show a high efficiency for the cross-linking collagen (see, for example, US Pat. Applic. No. 20040059430 (Ser. No. 10/618, 447). It has also been shown that the toxicity of polyepoxy compounds is lower than that of glutaraldehyde, and the antigenicity or immune-response induction of tissues decreases in proportion to the reaction time, in case of reacting with helical polypeptide molecules such as collagen. Naturally, it shows relatively good biocompatibility (see, for example, Lohre et al., (1992), Artif. Organs, 16:630-633; Uematsu et al., (1998), Artif. Organs, 22:909-913). Consequently, polyepoxy compounds as described are one preferred cross-linking agent.

In some embodiments, the cross-linking agent comprises about 1% glutaraldehyde and the length of exposure is at least about 24 hours. It will be appreciated that the time length for exposure of the biomaterial to the cross-linking agent depends on the agent used, the concentration and the temperature. Typically, the length of exposure is between 24 hours to 28 days. The determination of the precise amount of exposure time for the biomaterial to the cross-linking agent is well within the scope of a person skilled in the art.

Again, without wishing to be bound by any particular theory or hypothesis, the inventors consider that by exposing the biomaterial that has been exposed to alcohol to a cross-linking agent, the esterified carboxyl groups and amine groups on the collagen present in the biomaterial are cross-linked.

While it will be appreciated by those skilled in the art that the temperature at which each of the steps of the present invention is carried out is not critical, it will be understood that preferably, the temperature is between 2° C. and 40° C., more preferably, between 4° C. and 30° C. and most preferably, between 5° C. and 25° C.

Once again, after the cross-linking step, the biomaterial is preferably rinsed in rinsing solution such as that used after the alcohol exposure step (a). However, it will again be appreciated that the rinsing step is merely a preferment.

Following the cross-linking step, or if utilised the rinsing step after the cross-linking step, the biomaterial may then exposed to an acidic solution containing any acid capable of inactivating and/or modifying the fixed and/or unfixed cross-linking agent moieties present in the biomaterial after step (b) to remove or reduce available calcium binding sites. Alternatively, or in addition to, the acidic solution used in step (c) contains any acid capable of further cross-linking the activated carboxyl groups with the activated amine groups on the collagen to form amide bonds.

Preferably, the acidic solution comprises at least one aminocarboxylic acid. The term "aminocarboxylic acid" as used herein is any acid having at least one amino group and at least one carboxylic acid substituent. Representative examples of aminocarboxylic acids that are useful in the present invention include, but are not limited to, L-glutamate, L-aspartate, L-lysine L-arginine, L-histidine. The purpose of the acidic solution is two-fold: firstly, the aminocarboxylic acid assists in the inactivation and/or modification of the fixed and unfixed cross-linking agent moieties, thereby reducing or alleviating any adverse biological effects. Secondly, the aminocarboxylic acid further cross-links the activated carboxyl groups with the activated amine groups on the collagen to form amide bonds.

The concentration of the aminocarboxylic acid will depend upon the actual acid used and other parameters such as total mass of the biomaterial used and the like. In addition, a minimum wet weight ratio of aminocarboxylic acid to biomaterial would be about 1:4. The most important aspect of the acidic solution is the pH. The pH must be below pH7, preferably below pH6, more preferably below pH5 and most preferably below about pH4.6.

In one embodiment, the acidic solution is 8 mg aminocarboxylic acid per milliliter of de-ionised water, which is phosphate-free and about pH4.

The biomaterial is exposed to the aminocarboxylic acid for at least 6 hours, more preferably at least 24 hours, even more preferably more than 48 hours. While the incubation temperature is not critical it is preferably between 5° C. and 55° C., more preferably between 10° C. and 45° C., most preferably about 45° C.

In some embodiments, step (c) of the disclosed methods is replaced by or supplemented with a method of inhibiting the formation of metalloproteinase on elastin molecules present in the biomaterial. Specifically, in tissue such as aortic tissue a higher percentage of elastin is present than in other tissue. These elastin molecules can provide sites for the formation of metalloproteinase as such these sites need to be reduced, removed or inactivated. As shown in Example 1 infra, a buffer-free solution, containing a multi-valent cation such as magnesium, ferric and aluminium salts can be used to reduce the formation of metalloproteinase.

The biomaterial, after the step of exposing the biomaterial or collagen containing material to the acidic solution and/or buffer-free solution containing a multi-valent cation, is again preferably rinsed in rinsing solution. In some embodiments, the biomaterial is also sterilised.

The step of sterilising the biomaterial is by any method of sterilisation known in the art for collagen containing material. For example, the biomaterial may be subjected to a sterilising agent (e.g., a liquid sterilant such as 0.2-2.0% by weight glutaraldehyde solution) for a sterilisation time period. A 0.625% glutaraldehyde solution may be used in combination with heat (i.e. warming above room temperature, but below a temperature which would cause damage to the biomaterial), as the sterilant. Alternatively, a suitable sterilant solution may comprise an osmotically balanced aqueous solution alone or in combination with a non-contacting source of sterilisation (e.g., radiation, electron beam, UV, or other similar expedient), or include an aqueous solution of glutaraldehyde in combination with phosphate buffered saline. In instances where a 0.625% glutaraldehyde solution is used as the sterilant, the sterilisation time period may be 1-6 days at 37° C. or 1-2 days at 50° C.). This terminal sterilisation step may be performed after packaging of the biomaterial in its final container, thereby eliminating the need for any subsequent handling of the biomaterial until the time of implantation.

In one preferred embodiment, the biomaterial is sterilised by exposing the biomaterial to 0.25% glutaraldehyde in deionised water containing 9.07 g/l potassium di-hydrogen phosphate buffer.

The sterilisation step may be carried out for any length of time and may include storage. The temperature of sterilisation is preferably carried out between 40-50° C. for more than 60 minutes.

The biomaterial, after treatment with the methods disclosed herein, has a high level of resistance to calcification i.e. it is a "calcification-resistant biomaterial". The term "calcification" as used herein refers to one of the major pathological problems associated with traditionally produced biomaterial comprising connective tissue proteins (i.e., collagen and elastin). It has previously been shown that these materials can become calcified following implantation within the body. Such calcification can result in undesirable stiffening or degradation of the biomaterial. Two (2) types of calcification: intrinsic and extrinsic are known to occur in fixed collagenous biomaterial, although the exact mechanism(s) by which such calcification occurs is unknown. Intrinsic calcification is characterised by the precipitation of calcium and phosphate ions within the fixed bioprosthetic tissue, including the collagen matrix and remnant cells. Extrinsic calcification is characterised by the precipitation of calcium and phosphate ions within adherent thrombus, including adherent cells (e.g., platelets) to the biomaterial and the development of calcium phosphate-containing surface plaques on the biomaterial.

Consequently, the phrase "high level of resistance to calcification" or "calcification-resistant" when applied to the biomaterial of the present invention means that the biomaterial, after in vivo implantation for at least 200 days, shows less than 50 µg, preferably less than 20 µg, and even more preferably less than 10 µg of calcium per mg of dried tissue after its removal.

Preferably, the biomaterial of the present invention is also resistant to enzymatic degradation. The term "resistant to enzymatic degradation" as used herein refers to the ability of the biomaterial of the present invention to withstand enzymatic degradation to a comparable level with traditional fixed tissue.

Once formed, the implantable biomaterial or collagen containing material of the present invention can then be used to treat a number of conditions and/or disorders.

Generally, the terms "treating," "treatment" and the like are used herein to mean affecting an individual or animal, their tissue or cells to obtain a desired pharmacological and/or physiological effect. The effect is especially therapeutic in terms of a partial or complete cure of a condition and/or disorder. "Treating" as used herein covers any treatment of a condition and/or disorder in a vertebrate, a mammal, particularly a human, and includes: (a) inhibiting the condition and/or disorder, i.e., arresting its development; or (b) relieving or ameliorating the symptoms of the condition and/or disorder, i.e., cause regression of the symptoms of the enzymatic degradation/condition and/or disorder.

The terms "condition" and/or "disorder" are used herein interchangeably and refers to abnormal conditions affecting animals, including humans, which can be treated using the biomaterial of the present invention. Accordingly, the treatment of a wound, a lesion, tissue degeneration, a microbial infection, a burn, an ulcer, dermal condition is included in the present invention. Moreover, the replacement of heart valves, aortic roots, aortic wall, aortic leaflets, pericardial tissue, connective tissue, dura mater, dermal tissue, a vascular tissue, cartilage, pericardium, ligaments, tendon blood vessels, umbilical tissue, bone tissue, fasciae, and submucosal tissue are also encompassed.

The calcification-resistant biomaterial of the present invention may also be applied to any of a wide variety of contacting surfaces of medical devices. Contacting surfaces include, but are not limited to, surfaces that are intended to contact blood, cells or other bodily fluids or tissues of an animal, including specifically a human. Suitable contacting surfaces include one or more surfaces of medical devices that are intended to contact blood or other tissues. The medical devices include aneurysm coils, artificial blood vessels, artificial hearts, artificial valves, artificial kidneys, artificial tendons and ligaments, blood bags, blood oxygenators, bone and cardiovascular replacements, bone prostheses, bone waxes, cardiovascular grafts, cartilage replacement devices, catheters, contact lenses, containers for cell and tissue culture and regeneration, embolization particles, filtration systems, grafts, guide channels, in-dwelling catheters, laboratory instruments, microbeads, nerve-growth guides, ophthalmic implants, orthopedic implants, pacemaker leads, probes, prosthetics, shunts, stents, supports for peptides, surgical instruments, sutures, syringes, urinary tract replacements, wound coverings, wound dressings, wound healing devices and other medical devices known in the art.

Other examples of medical devices that would benefit from the application of the present invention will be readily apparent to those skilled in the art of surgical and medical procedures and are therefore contemplated by the instant invention. The contacting surface may include a mesh, coil, wire, inflatable balloon, or any other structure which is capable of being implanted at a target location, including intravascular locations, intralumenal locations, locations within solid tissue, and the like. The implantable device can be intended for permanent or temporary implantation. Such devices may be delivered by or incorporated into intravascular and other medical catheters.

The process of coating the surfaces of such devices can be performed by the plasma coating technique, as described in the International patent application No. WO96/24392.

In one preferred embodiment, the biomaterials of the present invention are used directly as wound dressings. For example, as described supra, the biomaterials can be dried and used as a wound dressing directly.

The wound dressings of the present invention are preferably in the form of a continuous sheet form, similar to wound dressings known in the art. However the invention may also take other particular conformations. For example, wound dressings of the present invention may be produced by cutting a desired design pattern from stock sheets of biomaterial described above. For example, the sheet may be die-cut from stock sheets of biomaterial.

In use, the wound dressings of the present invention are preferably used as the primary dressing placed in direct contact with the wound bed, or as near as practical against the wound bed. The dressings may serve as a packing material and, if required, may be secured into position with any suitable secondary wound dressing or device such as a wrap, tape, gauze, pad, suture or clip. The dressings may be temporary or permanent, and may be permanently incorporated into the healed tissues. When necessary, the wound dressings are changed by first removing any over-dressing material and then removing the dressing, whereby any accumulated necrotic tissue and exudate is lifted away. The temporary wound dressing of the present invention may be replaced by a fresh dressing or other suitable wound covering.

The dressings may be placed in their entirety into a wound. The dressings of the present invention may be cut, shaped and modified to accommodate numerous uses and applications.

A further use for the biomaterials of the present invention is in the delivery of therapeutically active agents including in any of the aforementioned applications. Therapeutically active agents may participate in, and improve, the wound healing process, and may include antimicrobial agents, including but not limited to anti-fungal agents, anti-bacterial agents, anti-viral agents and anti-parasitic agents, growth factors, angiogenic factors, anti-inflammatory agents, anti-thrombotic agents, anaesthetics, mucopolysaccharides, metals and other wound healing agents.

Examples of antimicrobial agents that can be used in the present invention include, but are not limited to, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ampicillin, amphotericin B, ketoconazole, fluconazole, pyrimethamine, sulfadiazine, clindamycin, lincomycin, pentamidine, atovaquone, paromomycin, diclazaril, acyclovir, trifluorouridine, foscarnet, penicillin, gentamicin, ganciclovir, iatroconazole, miconazole, Zn-pyrithione, heavy metals including, but not limited to, gold, platinum, silver, zinc and copper, and their combined forms including, salts, such as chloride, bromide, iodide and periodate, and complexes with carriers, and other forms.

Growth factor agents that may be incorporated into the wound dressing devices of the present invention include, but are not limited to, basic fibroblast growth factor (bFGF), acidic fibroblast growth factor (aFGF), nerve growth factor (NGF), epidermal growth factor (EGF), insulin-like growth factors 1 and 2, (IGF-1 and IGF-2), platelet derived growth factor (PDGF), tumor angiogenesis factor (TAF), vascular endothelial growth factor (VEGF), corticotropin releasing factor (CRF), transforming growth factors $\alpha$, and $\beta$ (TGF-$\alpha$ and TGF-$\beta$) interleukin-8 (IL-8); granulocyte-macrophage colony stimulating factor (GM-CSF); the interleukins, and the interferons.

Other agents that may be incorporated into the wound dressings of the present invention are acid mucopolysaccharides including, but not limited to, heparin, heparin sulfate, heparinoids, dermatan sulfate, pentosan polysulfate, cellulose, agarose, chitin, dextran, carrageenin, linoleic acid, and allantoin.

Examples of anti-inflammatory and anti-thrombotic agents include endomethycin, heparin, indomethacin, ibuprofen, aspirin, choline salicylate, diflunisal, magnesium salicylate, magnesium choline salicylate, salsalate, flurbiprofen, fenoprofen, ketoprofen, naprosyn, naproxen sodium, oxaprozin, diclofenac sodium, diclofenac misoprostol, etodolac, indocid, ketorolac, natumetone, sulindac, tolmetin, sulfinpyrazone, dipyridamole, ticlopidine, valdecoxib, rofecoxib, piroxicam, meloxicam, meclofenamate sodium, mefenamic acid, cyclophosphamide, cyclosporine micromulsion, chlorambucil, anagrelide, clopidogrel, and cilostazol; the anti-thrombic agent may be an anti-coagulant selected from the group consisting of heparin, ardeparin, and enoxaparin, tinzaparin, danaparoid, elpiruden and hirudin.

The therapeutically active agents may be bound, either physically or chemically, to the biomaterials of the present invention by methods well known in the art.

By "comprising" is meant including, but not limited to, whatever follows the word comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The invention will now be further described by way of reference only to the following non-limiting examples. It should be understood, however, that the examples following are illustrative only, and should not be taken in any way as a restriction on the generality of the invention described above. In particular, while the invention is described in detail in relation to the treatment of pericardium, valved aortic roots, valve leaflets and aortic wall tissues from bovine, porcine and marsupial sources, it will be clearly understood that the findings herein are not limited to these specific tissues or animal sources.

Example 1

Basic Processing of Biomaterial

Kangaroo hearts from adult Western grey kangaroos were harvested by a professional kangaroo shooter in Western Australia and transported to the laboratory on ice packs within 4-6 hours of death. The hearts were washed twice in ice-cold 0.9% saline solution. The pericardium was removed and carefully cleaned from adherent fat and loose connective tissue. The aortic roots with the aortic valves were dissected from the hearts and placed in ice-cold 0.9% saline containing 0.5 mM Phenyl-methyl-sulfonyl-fluoride (PMSF). The pericardium was stored overnight at 4° C. in ice-cold 0.9% saline containing 0.5 mM PMSF and the valved aortic roots washed for 20 minutes in the 0.9% saline solution containing PMSF.

A water-soluble alcohol-containing solution of 60-80% v/v by volume alcohol ethanol was prepared. The pericardium was immersed into the alcohol solution after overnight storage at 4° C. The valved aortic roots were immersed in the same alcohol solution immediately after the final wash in ice-cold 0.9% saline (containing 0.5 mM PMSF). The pericardium and the valved aortic roots were kept in the alcohol solution at about 5° C. for a minimum of 24 hours.

The pericardium and the valved aortic roots were removed from the alcohol solution and rinsed for about 10 minutes with 0.9% saline. During the rinsing period, the temperature of the rinsing solution was maintained at approximately 10° C.

The pericardium and the valved aortic roots were immersed in a 0.625% solution of glutaraldehyde containing 9.07 g/l potassium di-hydrogen phosphate buffer in sterile, deionised water. The pH of the glutaraldehyde solution was adjusted to 7.4 with sodium hydroxide. The pericardium and the valved aortic roots were fixed in the glutaraldehyde solution at 1-5° C. for a minimum period of 24 hours to crosslink proteins present in the collagen of the tissues.

The pericardium and the valved aortic roots were removed from the glutaraldehyde solution and rinsed in a sterile 0.9% sodium chloride for about 15 minutes. During the rinsing period, the temperature of the rinsing solution was maintained at approximately 10° C.

The pericardium and the valved aortic roots were then treated by two alternative procedures. In the first procedure, the pericardium and the valved aortic roots were immersed in a buffer-free solution containing 8 mg dicarboxylic acid per 1 ml de-ionised water volume. The pH of the solution was adjusted to a pH of 4.5 with a volume of diluted hydrochloric acid. The pericardium and the valved aortic roots were immersed in the solution at a temperature of about 45° C. for about 48 hours.

In the second procedure the pericardium and the valved aortic roots were immersed in a buffer-free solution, containing a multi-valent cation such as magnesium, ferric and aluminium salts, dissolved in de-ionised water, at a pH 3.5 for about 60 minutes.

The biomaterial was then sterilized either by immersing the tissue in a 0.25% solution of glutaraldehyde containing 9.07 g/l potassium di-hydrogen phosphate buffer in sterile, deionised water. The pH of the aldehyde solution was adjusted to 7.4 with sodium hydroxide. The process of sterilization was carried out at a temperature about 45° C. for about 120 minutes.

Alternatively, the biomaterial was sterilized in an aqueous solution comprising 2% Epoxypropane combined with 20% ethyl alcohol by weight at 37° C. for about 24 hours. The sterilised tissue was then stored in 0.2% buffered glutaraldehyde plus 15% isopropanol.

Example 2

Effect of Temperature on the Biomaterial

Denaturation temperature is an important measure of cross-linking stability and it reflects material strength, durability and integrity.

Bovine pericardium was obtained from a local abattoir in Western Australia and transported to the laboratory on ice. The pericardium was cleaned as described in Example 1.

The degree of cross-linking of bovine pericardium as prepared according to the methods described in Example 1, was compared with bovine pericardium fixed in 0.625% buffered glutaraldehyde (Control Pericardium).

Representative pericardial sample strips (5×10 mm) in each group were attached to an isometric force transducer (MLT0500, AD Instruments, Australia), interfaced with a PowerLab data acquisition system and a desktop personal computer. Samples were kept in constant extension with a load of 90±5 g and immersed in an open, temperature controlled water bath filled with 0.9% saline. The temperature of the water bath was gradually increased at approximately 1.5° C./min from 25° C. to 95° C. Shrinkage temperature was indicated at a sharp deflection point from constant extension when the collagenous material was denatured. Results (shrinkage temperature expressed as degrees Celsius) are summarised in Table I.

TABLE I

| Type of tissue: | Number | Shrinkage Temperature |
|---|---|---|
| Control Pericardium | 10 | 84.10 ± 0.17 |
| Treated Pericardium | 10 | 85.54 ± 0.15 |

Example 3

Enzymatic Degradation of Biomaterial

The level of resistance to enzymatic degradation of bovine pericardium, prepared according to the methods described in Example 1 (treated pericardium), was compared with bovine pericardium fixed in 0.625% buffered glutaraldehyde (control pericardium).

A pronase solution was prepared by dissolving 100 mg pronase (*Streptomyces griseus*) and 100 mg calcium chloride, in 200 ml of HEPES buffer solution (0.01M, pH7.4), containing 0.1M glycine. Fixed tissue samples were rinsed in deionised water for 3 minutes, blotted, dried overnight at 70° C. and weighed. These samples were incubated in the pronase solution at 50° C. for 24 hours. Remaining tissue samples were rinsed in deionized water dried overnight at 70° C. and weighed. Resistance to pronase digestion was determined by the mass of remaining tissue, expressed as a percentage of pre-digested tissue mass. Results are summarised in Table II.

TABLE II

| Type of tissue | Number of samples | % Remaining Tissue |
|---|---|---|
| Control Pericardium | 10 | 81.98 ± 1.97 |
| Treated Pericardium | 10 | 89.13 ± 0.39 |

Example 4

Tensile Strength of Biomaterial

Tensile strength is an important measure of material strength and reflects durability of cross-linked tissues.

The tensile strength of bovine pericardium, prepared according to the methods described in Example 1 (treated pericardium), was compared with bovine pericardium fixed in 0.625% buffered glutaraldehyde (control pericardium).

Tensile strength of representative pericardial strips (8×80 mm) of both groups of tissue were measured with a hydraulic Zwick/Roell (Model 2010) tensile testing machine, fitted with a 10 kNewton load-cell at a constant extension rate of 50 mm/min. Tensile strength and elongation at break were evaluated from the recorded load/elongation curves. Results are summarized in Table III.

TABLE III

| Type of tissue | Number of samples | Tensile strength (N/mm$^2$) | Elongation (%) |
|---|---|---|---|
| Control Pericardium | 10 | 36.59 ± 1.33 | 14.18 ± 1.67 |
| Treated Pericardium | 10 | 71.82 ± 3.33 | 15.99 ± 0.61 |

Example 5

Calcification Profile of Biomaterial

Experimental studies in small and large animal models have been performed to assess the effectiveness of the above-described process in mitigating calcification of treated collagen containing biomaterials.

In the first animal study, kangaroo valve leaflets and kangaroo aortic wall tissues, prepared by standard fixation in only 0.625% buffered glutaraldehyde (untreated tissue), were compared with kangaroo valve leaflets and kangaroo aortic wall tissues treated according to the methods described in Example 1 (treated tissue).

Aortic wall tissue samples (10×5 mm size) and aortic valve leaflets of both groups were rinsed in 0.9% saline for 5 minutes. The rinsed tissues were surgically implanted in subcutaneous pockets (one sample of each group per rat), created in the central dorsal wall area of growing (6 weeks old) male Wistar rats. After 60 days, the explanted tissues were dissected out of surrounding host tissue and dried in a Biotherm incubator (Selby Scientific, Perth, Wash.) at 90° C. for 48 h. The dried samples were weighed, and the calcium content extracted in 5.0 ml 6 N ultrapure hydrochloric acid (Merck, Perth, Wash.) at 75° C. for 24 h. The extractable calcium content was then measured using an atomic absorption spectrophotometer (Varian AA1275) and expressed as μg calcium per mg tissue (dry weight). These data are summarised in Table IV.

TABLE IV

| Type of Tissue | Number | Untreated Tissue | Treated Tissue |
|---|---|---|---|
| Valve leaflet | 10 | 6.45 ± 4.65 | 1.3 ± 0.74 |
| Aortic wall | 10 | 28.67 ± 7.22 | 1.9 ± 0.15 |

The effectiveness of the new process in mitigating calcification is readily apparent in Table IV. Calcium levels in the treated tissues were comparable to levels normally present in unfixed tissues and therefore demonstrate the superiority of the new process compared to standard glutaraldehyde fixation only.

Example 6

Further Calcification Studies in Sheep

In a further animal study, kangaroo valved aortic conduits, fixed in 0.625% buffered glutaraldehyde as described in Example 1 (treated tissue) were compared with valved aortic roots extracted as in Example 1 (untreated tissue). The aortic roots were rinsed in 0.9% saline for 5 minutes and surgically implanted in the pulmonary artery position of juvenile (4 months old) Merino-Dorset crossbred sheep. These valved implants were removed after 200 days and the calcium content of the valve leaflets and aortic wall tissues determined by atomic absorption spectrophotometry as described above.

Results (μg Calcium per mg dried tissue) are summarised in Table V.

TABLE V

| Type of Tissue | Number | Untreated Tissue | Treated Tissue |
|---|---|---|---|
| Valve leaflet | 12 | 2.54 ± 1.30 | 1.20 ± 0.94 |
| Aortic wall | 12 | 137.93 ± 12.68 | 3.22 ± 0.75 |

Example 8

Further Calcification Studies with Pig-Derived Tissue

In a further animal study, untreated porcine aortic valved conduits, fixed in buffered 0.625% glutaraldehyde (untreated tissue) were compared with porcine valved conduits prepared according to the method described in Example 1 (treated tissue). The porcine valved conduits were rinsed in 0.9% saline for 5 minutes and surgically implanted in the pulmonary artery position of juvenile (4 months old) Merino-Dorset crossbred sheep. These valved implants were removed after 200 days and the calcium content of the valve leaflets and aortic wall tissues determined by the atomic absorption spectrophotometry described supra.

Results (μg Calcium per mg dried tissue) are summarised in Table VI.

TABLE VI

| Type of Tissue | Number | Untreated Tissue | Treated Tissue |
|---|---|---|---|
| Valve leaflet | 6 | 40.68 ± 5.39 | 3.60 ± 1.75 |
| Aortic wall | 5 | 142.62 ± 14.25 | 5.54 ± 1.99 |

Example 8

Calcification of Bovine Pericardium

In a further animal study, the calcification potential of bovine pericardium fixed in 0.625% buffered glutaraldehyde (control pericardium) was compared with the calcification potential of bovine pericardium prepared according to the method described in Example 1 (treated pericardium). Representative samples of each group were trimmed to 1×1 cm size and rinsed in 0.9% saline for 5 minutes. These samples were surgically implanted in subcutaneous pockets, created in the central dorsal wall area of growing (6 weeks old) male Wistar rats. These tissues were removed after 60 days, host tissue removed and the calcium content determined by atomic absorption spectrophotometry. Results (μg Calcium per mg dried tissue) are summarised in Table VII.

TABLE VII

| Type of tissue | Number | Calcium Content |
|---|---|---|
| Control Pericardium | 10 | 136.68 ± 11.39 |
| Treated Pericardium | 10 | 4.10 ± 2.11 |

Example 10

Calcification of Decellularized Kangaroo Pericardium

In another animal study, the calcification potential of kangaroo pericardium fixed in 0.625% buffered glutaraldehyde (control pericardium) was compared with the calcification potential of kangaroo pericardium, which had been decellularized and prepared according to the methods described in Example 1 (treated pericardium).

Represented samples of each group were trimmed to 1×1 cm size and rinsed in 0.9% saline for 5 minutes. These samples were then surgically implanted in subcutaneous pockets, created in the mid-abdominal dorsal wall area of growing (6 weeks old) male Wistar rats. These tissues were removed after 60 days, host tissue removed and the calcium content determined by atomic absorption spectrophotometry by standard procedures. Results (μg calcium per mg dried tissue) are summarised in Table VIII.

TABLE VIII

| Type of Tissue | Number | Calcium Content |
|---|---|---|
| Control Pericardium | 5 | 2.440 ± 0.600 |
| Treated Pericardium | 7 | 0.406 ± 0.029 |

Example 11

Recellularization of Decellularized Kangaroo Pericardium

In the sixth animal study, the recellularization potential of decellularized kangaroo pericardium fixed in 0.625% buffered glutaraldehyde (control pericardium) was compared with the recellularization potential of decellularized kangaroo pericardium prepared according to the method described in Example 1 (treated pericardium). The kangaroo pericardium was decellularized for 24 hours at room temperature in 0.25% Triton x-100 and 0.25% Sodium dodecyl sulfate and rinsed in culture media for 20 minutes. Represented samples (n=5) of each group of pericardium were trimmed to 2×2 cm size and rinsed in 0.9% saline for 5 minutes. These samples were seeded under sterile conditions with $3.0 \times 10^5$ human fibroblasts/cm², harvested from human saphenous vein. The seeded pericardium was incubated at 37° C. in standard static cell culture conditions for 21 days. Cell growth was microscopically assessed every 7 days and categorised according to the following a visual scale of:

1). No viable fibroblasts present on matrix surface;
2). Less than 50% of matrix surface covered with fibroblasts (+);
3). More than 50% matrix surface covered with fibroblasts (++);
4). Matrix completely covered by multiple layers of fibroblasts (+++).

A rapid colorimetric assay, MTT (3-[4,5-dimethylthiazol-2-yl]-2,5diphenyltertra-zolium bromide test was employed at day 21 to confirm the absence of viable fibroblasts on the control pericardium and presence of viable fibroblasts on the treated pericardium (for MTT method see, for example, Zund et al., 1999, *Eur J Cardiothorac Surg.*, 15(4):519-24). Results are summarised in Table IX.

TABLE IX

| Time | Control Pericardium | | | | | Treated Pericardium | | | | |
|---|---|---|---|---|---|---|---|---|---|---|
| Day 0 | + | + | + | + | + | + | + | + | + | + |
| Day 7 | + | 0 | 0 | 0 | 0 | + | ++ | + | ++ | ++ |
| Day 14 | 0 | 0 | 0 | 0 | 0 | ++ | +++ | ++ | +++ | +++ |
| Day 21 | 0 | 0 | 0 | 0 | 0 | +++ | +++ | ++ | +++ | +++ |

Example 12

Crosslink Stability of Kangaroo Tissue

Figure 2:
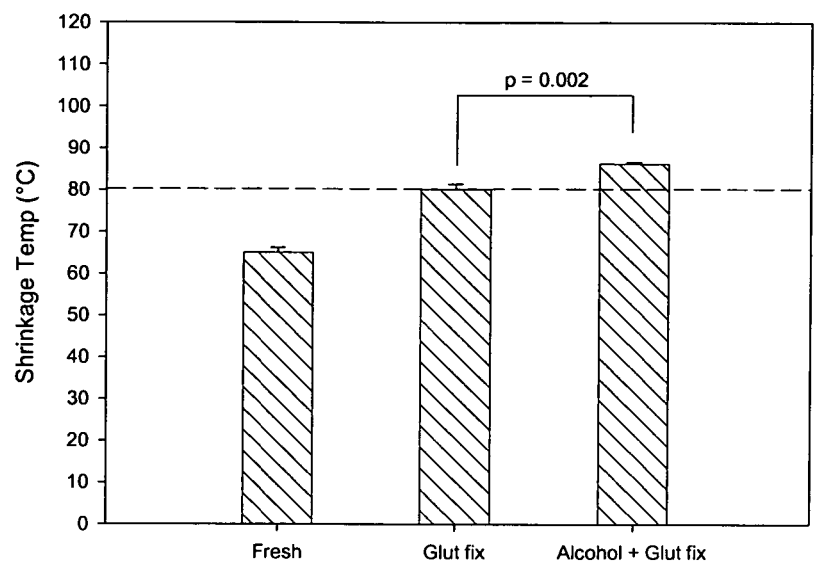
FIG. 2 shows kangaroo aortic tissue that was pre-treated with alcohol then glutaraldehyde fixed compared to glutaraldehyde fixed tissue i.e. no alcohol pre-treatment and "fresh" tissue.

Two types of kangaroo tissue, aortic wall tissue and kangaroo pericardium, were treated using the procedure outlined in Example 1 up to and including step (b) i.e. alcohol-solution pretreatment and then glutaraldehyde cross-linking. These treated tissues were then compared to glutaraldehyde fixed tissue i.e. no alcohol pre-treatment and "fresh" tissue. FIG. 1 and FIG. 2 show the cross-linking stability of pericardium (FIG. 1) and aortic wall tissue (FIG. 2). It can be seen that pre-treatment with ethanol has a significant affect on the stability of the cross-linking at ~85° C.-86° C. These data can also be seen in Table X.

TABLE X

| CROSSLINK STABILITY - KANGAROO PERICARDIUM Shrinkage Temp (° C.) : n = 5 | |
|---|---|
| Fresh | 66.55 ± 1.200 |
| Glutaraldehyde fixed | 80.74 ± 1.047 |
| Alcohol + Glutaraldehyde fixation | 84.62 ± 0.465 | p = 0.016 (Glut fix versus alcohol + glut fix)

| CROSSLINK STABILITY - KANGAROO DESC AO WALL Shrinkage Temp (° C.) : n = 5 | |
|---|---|
| Fresh | 65.00 ± 1.423 |
| Glutaraldehyde fixed | 80.11 ± 1.281 |
| Alcohol + Glutaraldehyde fixation | 86.21 ± 0.449 | p = 0.002 (Glut fix versus alcohol + glut fix)

Example 13

Crosslink Stability and Calcification Behaviour in a Subcutaneous Rat Model

This study aimed to compare the crosslink stability and calcification behaviour of porcine tissue (cusp and wall), treated with the method disclosed in Example 1 as compared to a glutaraldehyde-fixed tissue control and commercially prepared Freestyle® and PrimaPlus® bioprosthetic tissues.

Fresh porcine valved aortic roots were harvested and transported at 4° C. in phosphate-buffered saline (PBS; 0.1M, pH7.4). Representative aortic valve cusps (n=30) and aortic wall samples (n=30; 10 mm×15 mm) were removed from the aortic roots and divided into two groups. Group I included valve cusps (n=15) and representative aortic wall samples (n=15; 10 mm×15 mm) stored in 0.25% buffered glutaraldehyde. Group II included valve cusps (n=15) and representative aortic wall samples (n=15; 10 mm×15 mm) exposed to the method disclosed in Example 1 and stored in 0.25% buffered glutaraldehyde. For comparison, a third group (III) consisted of valve cusps (n=10) and aortic wall samples (n=10; 10 mm×15 mm) from Freestyle® bioprostheses, while group IV consisted of valve cusps (n=10) and aortic wall tissue (n=10; 10 mm×15 mm) from Prima Plus® bioprostheses.

Shrinkage temperature measurement was used to assess the stability of the collagen cross-links of the tissue (Levy et al., 1986, *Am. J. Pathol.*, 122:71-82). Cusp and aortic wall sample tissue strips (5×10 mm; n=10) in each group were attached to an isometric force transducer (MLT0500; AD Instruments, Australia), interfaced with a PowerLab data acquisition system and a desktop personal computer.

Samples were kept in constant extension with a load of 90±5 g and immersed in an open, temperature-controlled water bath filled with 0.9% saline. The temperature of the water bath was gradually increased at approximately 1.5° C. min from 25° C. to 95° C. The shrinkage temperature was indicated as a sharp deflection point from constant extension when the collagenous material was denatured.

The shrinkage temperatures for valve cusps and aortic wall tissues are listed in Table XI. No significant differences were identified between the control, test procedure of Example 1 ("test"), Freestyle® and Prima Plus® cusps. Test procedure—treated aortic wall tissue showed a significantly ($p<0.05$) higher shrinkage temperature compared to control, Freestyle® and Prima Plus® wall tissues.

TABLE XI

SHRINKAGE TEMPERATURES (° C.) OF VALVE CUSP AND AORTIC WALL TISSUE

| Sample | Cusp | Aortic wall |
|---|---|---|
| Control | 84.6 ± 1.40 | 86.73 ± 0.26 |
| Test | 85.5 ± 0.24 | 89.34 ± 0.19* |
| Freestyle | 85.7 ± 0.35 | 86.16 ± 0.40 |
| Prima Plus | 84.3 ± 0.18 | 86.37 ± 0.34 |

(n = 10 per group)
Values are mean ± SE.
*$p <0.05$ (Test versus Control, Freestyle, Prima Plus).

Resistance to proteolytic enzyme digestion was based upon the method of Girardot & Girardot (*J. Heart Valve Dis.*, 1996, 122: 71-82). A pronase solution was prepared by dissolving 10 mg pronase E (type XIV from *Streptomyces griseus*; Sigma) and 100 mg calcium chloride, in 200 ml HEPES buffer solution (0.01M, pH7.4), containing 0.1M glycine. Fixed tissue samples were rinsed in deionized water for 3 min, blotted, dried overnight at 70° C. and weighed. These samples were then incubated in pronase solution at 50° C. for 24 h. Remaining tissue samples were rinsed in deionized water, dried overnight at 70° C. and weighed. Resistance to pronase digestion was determined by the mass of remaining tissue, expressed as a percentage of the pre-digested tissue mass.

Figure 3A:
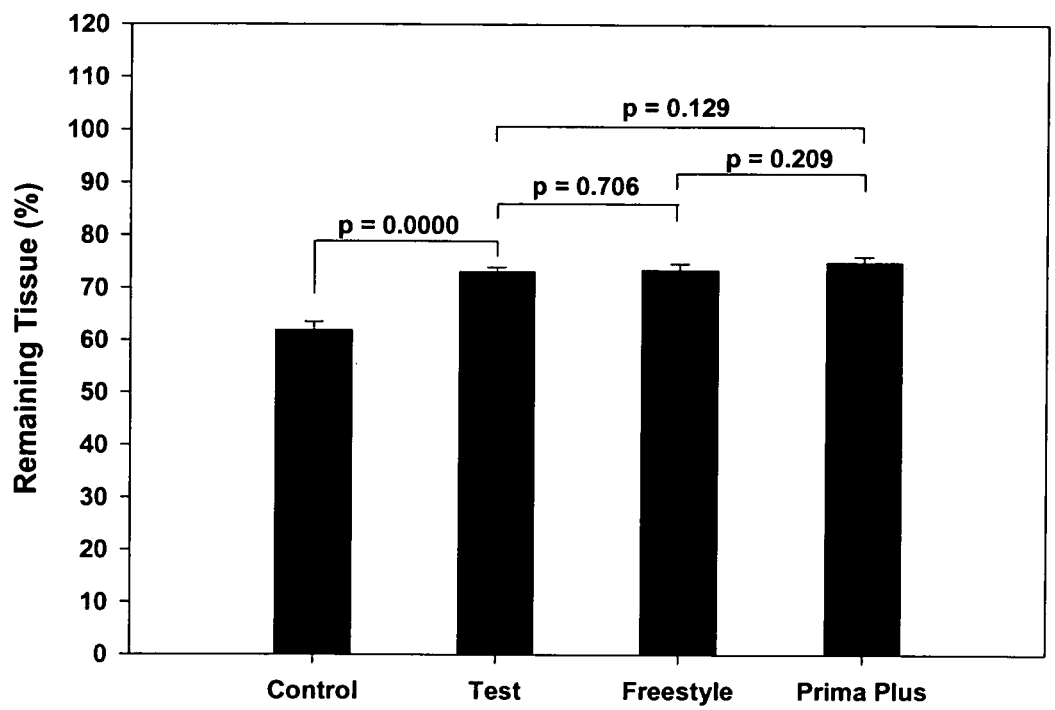
FIG. 3 shows the resistance to enzymatic degradation of (A) porcine cusp and (B) aortic wall tissues.

Resistance to enzymatic degradation is illustrated in FIG. 3. Test procedure, Freestyle® and Prima Plus® cusp tissues showed significant ($p<0.0001$) increases in resistance to proteolytic digestion compared to control (FIG. 3A). No significant difference was seen between test procedure, Freestyle® and Prima Plus® cusp tissues.

Figure 3B:
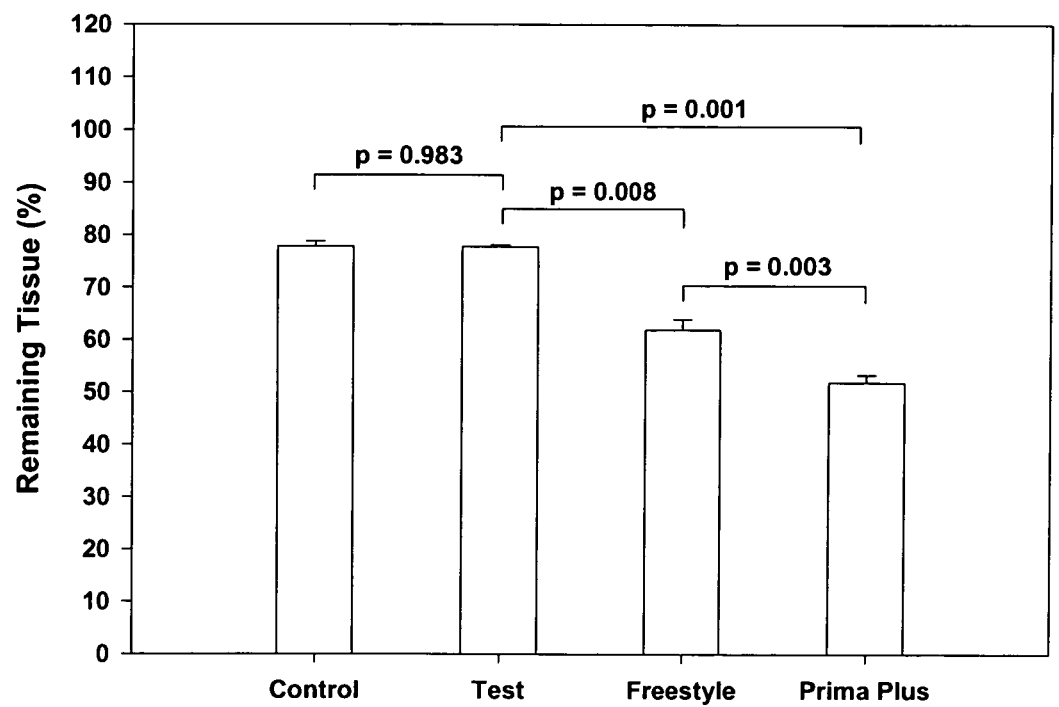

Test procedure-treated aortic wall tissue showed equal resistance (p=NS) to proteolytic digestion as the control tissue, and a significantly ($p<0.01$) higher resistance compared to Freestyle® and Prima Plus® wall tissues (FIG. 3B).

Young, male Wistar rats (bodyweight 150-200 g) were divided into two groups; one group (n=10) received cusp implants and the second group (n=10) received aortic wall implants. Each animal received one sample of each of the four groups of tissues, making a total of 80 implants.

Rats were anesthetized with pentobarbital (Nembutal®; 45 mg/kg, intraperitoneal). The dorsal muscle area was shaved and disinfected with 15% diluted chlorhexidine gluconate (ICI Pharmaceuticals, Perth, Wash.) and ethanol (Merck Chemicals, Perth, Wash.).

Implants were thoroughly rinsed in deionized water for 2 min to eliminate residual fixative, and then implanted into subcutaneous pouches through an incision of 2.5 cm into the back muscle wall. The incision was closed with 5-0 Prolene sutures.

Rats were sacrificed after eight weeks with an overdose of barbiturates (Euthenase®), and the dorsal muscle wall, containing the subcutaneous implants, was removed for quantitative and qualitative tissue calcium analysis. Each retrieved sample was divided into two anatomically symmetrical halves. One half was used for atomic absorption spectrophotometry, and the other half was fixed in 10% buffered formaldehyde and processed for histology.

Fixed samples were embedded in paraffin wax, sectioned at 3 μm, and treated with Von Kossa stain for qualitative calcium analysis. Histological examinations were performed using an Olympus BHS light microscope.

Explanted tissue samples from all groups were dissected free of surrounding host tissue and dried in a Biotherm incubator (Selby Scientific, Perth, Wash.) at 90° C. for 48 h. The dried samples were weighed, and the calcium content extracted in 5.0 ml 6 N ultrapure hydrochloric acid (Merck, Perth, Wash.) at 75° C. for 24 h. The extractable calcium content was measured using an atomic absorption spectrophotometer (Varian AA1275) and expressed as μg Ca per mg tissue (dry weight).

Histological examination indicated the presence of severe, intrinsic calcification in the explanted control cusp samples (data not shown). No visible calcification was noted in either the ADAPT, Freestyle or Prima Plus valve cusps (data not shown).

Explanted aortic wall tissue revealed several calcifications of the media ((data not shown) in control samples. No visible calcification was noted in the explanted test aortic wall tissue ((data not shown). Moderate calcification of the media was noted in the explanted Freestyle (data not shown) and Prima Plus (data not shown) aortic wall tissues.

Figure 4A:
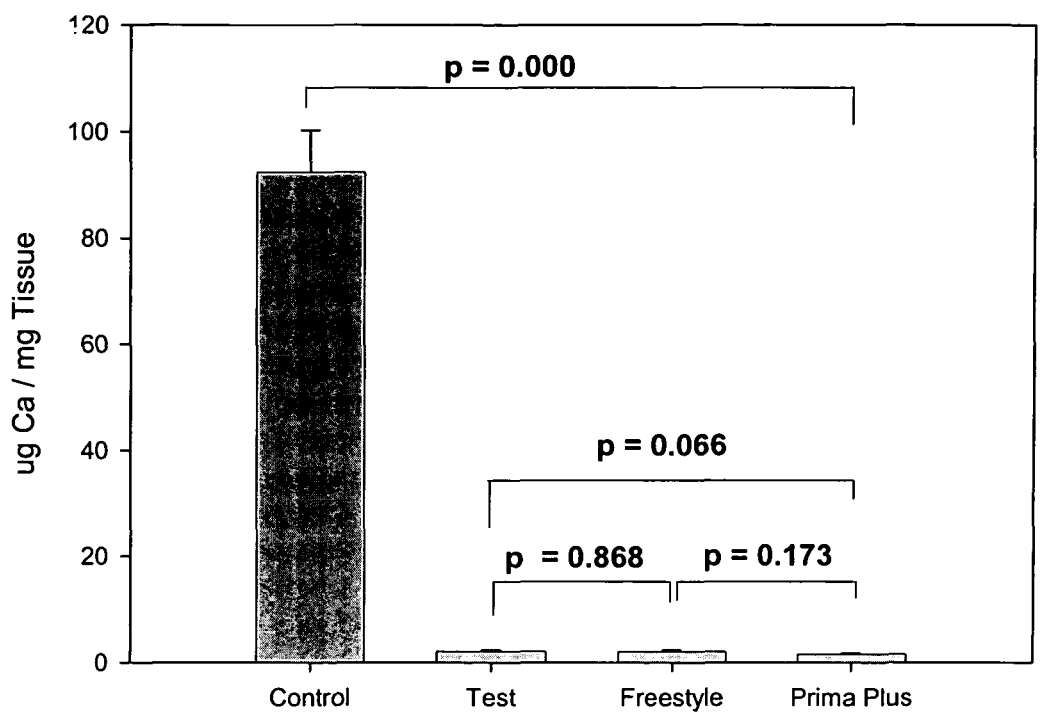
FIG. 4 shows the quantitative calcium levels of (A) explanted porcine valve cusps and (B) porcine aortic wall tissue after eight weeks in a subcutaneous rat model.

The quantitative tissue calcium levels for explanted cusps are illustrated in FIG. 4A. Control samples, fixed in glutaraldehyde only, showed the highest level of calcium in this model (92.37±7.9 μg/mg). The calcium levels of the tissue treated by the method of Example 1 were 2.09±0.22 μg/mg tissues, while Freestyle® was 2.03±0.29 μg/mg and Prima Plus® was 1.54±0.17 μg/mg. This means that the treated cusps significantly reduced calcium levels ($p<0.001$) compared to control samples. No significant difference was seen between the tissue calcium levels of Example 1, Freestyle® and Prima Plus® cusps after eight weeks.

Figure 4B:
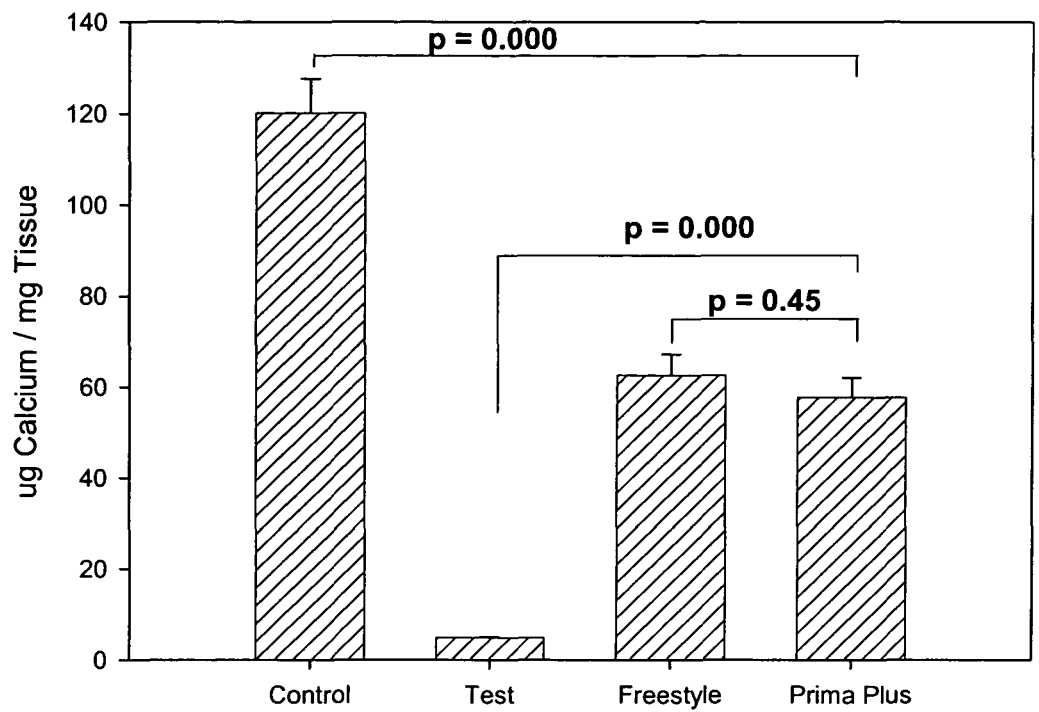

The quantitative tissue calcium levels for explanted aortic wall samples are illustrated in FIG. 4B. The calcium content of Example 1-treated aortic wall samples (4.86±0.12 µg/mg tissue) was significantly (p<0.001) lower by (95.9%) than that of control samples (120.11±7.48 µg/mg tissue). Freestyle® and Prima Plus® aortic wall samples showed reductions in calcification of 47.8% and 51.95%, respectively.

These data suggest that the method disclosed in Example 1 is effective in reducing the calcification in both porcine cusp and wall tissues in a subcutaneous rat model. These data further suggest that enhanced cross-linking plays an important role in minimizing aortic wall calcification.

The invention claimed is:

1. A method for producing a collagen containing calcification resistant implantable biomaterial comprising:
    (a) exposing a collagen containing material to a solution containing one or more $C_1$-$C_6$ water soluble lower alcohols at a temperature of about 5° C. for at least 24 hours;
    (b) removing said collagen containing material from said solution in step (a) and exposing said material to a cross-linking agent; and
    (c) removing said collagen containing material from said cross-linking agent in step (b) and exposing said material to a buffer-free acidic solution containing an aminocarboxylic acid at a temperature between 5° C. and 55° C. for at least 6 hours to produce said calcification resistant implantable biomaterial;
    wherein the collagen containing material used in step (a) has not been previously cross-linked.

2. The method of claim 1, further comprising a rinsing step between steps (a) and (b) and/or between steps (b) and (c) with a non-buffered physiologically acceptable solution.

3. The method of claim 1, further comprising a rinsing step after step (c).

4. The method of claim 3, wherein the step of rinsing the material is conducted using a phosphate-free saline solution.

5. The method of claim 3, wherein the step of rinsing the material is conducted at a temperature of approximately 10° C.

6. The method of claim 1, wherein the collagen containing material is isolated from an animal selected from the group consisting of an ovine, a bovine, a caprine, an equine, a porcine, a marsupial, and a human.

7. The method of claim 1, wherein the collagen containing material in step (a) is a cellular tissue selected from the group consisting of cardiovascular tissue, pelvic floor tissue, heart tissue, heart valve, aortic roots, aortic wall, aortic leaflets, peritoneum, pericardial tissue, connective tissue, the matrix of soft or solid organs, dura mater, dermal tissue, a vascular tissue, cartilage, pericardium, ligament, tendon, blood vessels, umbilical tissue, bone tissue, fasciae, submucosal tissue, and skin.

8. The method of claim 1, wherein the $C_1$-$C_6$ water-soluble lower alcohol is selected from the group consisting of methanol, ethanol, cyclohexanol, isopropanol, propanol, butanol, pentanol, isobutanol, sec-butanol, t-butanol, and combination thereof.

9. The method of claim 1, wherein the solution containing one or more $C_1$-$C_6$ water-soluble lower alcohols comprises less than 100% alcohol in a non-buffered aqueous solvent.

10. The method of claim 1, wherein step (a) is carried out for at least 48 hours.

11. The method of claim 1, wherein the cross-linking agent is selected from the group consisting of carbodiimide, polyepoxy ethers, divinyl sulfone (DVS), genipin, polyaldehyde, diphenylphosphoryl azide (DPPA), and combinations thereof.

12. The method of claim 11, wherein the polyaldehyde is glutaraldehyde.

13. The method of claim 1, further comprising a sterilisation step after step (c).

14. The method of claim 1, wherein the temperature of step (c) is about 45° C.

15. The method of claim 1, wherein the aminocarboxylic acid is selected from the group consisting of L-histidine, L-arginine, L-lysine, L-glutamate and L-aspartate.

16. The method of claim 1, wherein said collagen containing calcification resistant biomaterial has a calcium content of less than about 50 µg per mg of biomaterial and wherein said biomaterial is capable of being implanted for at least 200 days without the biomaterial increasing its calcium content above 50 µg/mg of biomaterial.

17. The method of claim 16, wherein said collagen containing calcification resistant biomaterial before implantation has a calcium content of less than 20 µg per mg of biomaterial.

18. The method of claim 16, wherein said collagen containing calcification resistant biomaterial before implantation has a calcium content of less than 10 µg per mg of biomaterial.

19. A method for producing a collagen containing calcification resistant implantable biomaterial comprising:
    (a) exposing a collagen containing material to a solution containing one or more $C_1$-$C_6$ water-soluble lower alcohols at a temperature of about 5° C. for at least 24 hours;
    (b) removing said collagen containing material from said solution in step (a) and exposing said material to a cross-linking agent;
    (c) removing said collagen containing material from said solution in step (b) and exposing said material to a buffer-free solution containing one or more multi-valent cation; and
    (d) removing said collagen containing material from said solution in step (c) and exposing said material to a buffer-free acidic solution containing an aminocarboxylic acid at a temperature between 5° C. and 55° C. for at least 6 hours to produce said calcification resistant implantable biomaterial;
    wherein the collagen containing material used in step (a) has not been previously cross-linked.

20. The method of claim 19, wherein the multi-valent cation is selected from the group consisting of magnesium, ferric and aluminium salts.

21. The method of claim 19, wherein said collagen containing calcification resistant biomaterial has a calcium content of less than about 50 µg per mg of biomaterial and wherein said biomaterial is capable of being implanted for at least 200 days without the biomaterial increasing its calcium content above 50 µg/mg of biomaterial.

22. The method of claim 21, wherein said collagen containing calcification resistant biomaterial before implantation has a calcium content of less than 20 µg per mg of biomaterial.

23. The method of claim 21, wherein said collagen containing calcification resistant biomaterial before implantation has a calcium content of less than 20 µg per mg of biomaterial.

24. A method for producing a collagen containing calcification resistant implantable biomaterial said method consisting essentially of:
    (a) exposing a collagen containing material to a solution containing one or more $C_1$-$C_6$ water soluble lower alcohols at a temperature of about 5° C. for at least 24 hours;
    (b) removing said collagen containing material from said solution in step (a) and rinsing said collagen containing material with a non-buffered physiologically acceptable solution at a temperature of approximately 10° C.;
(c) exposing said collagen containing material to a cross-linking agent; and
(d) removing said collagen containing material from said cross-linking agent in step (b) and rinsing said collagen containing material with a non-buffered physiologically acceptable solution at a temperature of approximately 10° C.;
(e) exposing said collagen containing material to a buffer-free acidic solution containing an aminocarboxylic acid at a temperature of about 45° C. for at least 6 hours; and
(f) removing said collagen containing material and rinsing with a phosphate-free saline solution to produce said calcification resistant implantable biomaterial,
wherein the collagen containing material used in step (a) has not been previously cross-linked.

* * * * *